United States Patent [19]

Fischbach

[11] Patent Number: 5,237,056
[45] Date of Patent: Aug. 17, 1993

[54] DNA ENCODING A PROTEIN WHICH COPURIFIES WITH ACETYLCHOLINE RECEPTOR INDUCING ACTIVITY AND USES THEREFOR

[75] Inventor: Gerald D. Fischbach, Cambridge, Mass.

[73] Assignee: President and Fellows of Harvard College, Cambridge, Mass.

[21] Appl. No.: 706,872

[22] Filed: May 29, 1991

[51] Int. Cl.$^5$ ............................................. C12N 15/12
[52] U.S. Cl. .................................. 536/23.5; 435/69.1; 435/240.1; 435/320.1
[58] Field of Search .............. 536/27; 435/69.1, 320.1, 435/240.1

[56] References Cited

PUBLICATIONS

Powels et al. from "Cloning Vectors" VIII-1 through 7, 1985.

Hunkapiller et al. Methods in Enzymology 91 pp. 227-236, 1983.

Suggs et al. Proc. Natl. Acad. Sci. USA 78(11) pp. 6613-6617, Nov. 1981.

"Purification and Characterization of a Polypeptide from Chick Brain that Promotes the Accumulation of Acetylcholine Receptors in Chick Myotubes", *J. Cell. Biol.* 103:493-507 (1986), Usdin, T. B. and Fischbach, G. D.

"Acetylcholine Receptor-Inducing Factor From Chicken Brain Increases the Level of mRNA Encoding the Receptor a Subunit", *Proc. Natl. Acad. Sci. USA* 85:1983-1987 (1988), Harris, D. A., et al.

Harris, D. A., et al., "Further Characterization of An Acetylcholine Receptor-Inducing Protein and Development of an Oligonucleotide Probe for this Molecule", *Society for Neuroscience Abstracts* (19th Annual Meeting, Phoenix, AZ, Oct. 29 to Nov. 3, 1989) 15 (Part 1):Abstract 70.6.

Falls, D. L., et al., "$M_r$ 42,000 ARIA:A Protein That May Regulate the Accumulation of Acetylcholine Receptors at Developing Chick Neuromuscular Junctions", *Cold Spring Harbor Symposia on Quantitative Biology* 55:397-406 (published Nov. 1991 according to Cold Spring Harbor Press).

Oesch, B. et al., "A Cellular Gene Encodes Scrapie PrP Protein", *Cell* 40:735-746 (1985).

*Primary Examiner*—Robert J. Hill, Jr.
*Assistant Examiner*—Nina Ossanna
*Attorney, Agent, or Firm*—Hamilton, Brook, Smith & Reynolds

[57] ABSTRACT

Described herein is the cloning and characterization of DNA encoding a protein which appears at an early stage in spinal cord development, is concentrated in motor neurons, and appears to have a role in neuromuscular junction formation. This protein copurifies with an activity which induces acetylocholine receptor synthesis in muscle fibers. A method for enhancing neurotransmitter receptor synthesis or accumulation in cells, especially that of the acetylcholine receptor, is also described.

2 Claims, 6 Drawing Sheets

```
                                                                     GAATTCCCTCGGC    -159
AGCCAGCTCCTCCCTCTCGCTATTATTCCTTCTCCCCCCCTAGCTGGATCATCTCAAGCCGAGCGGTGA    - 80
CGGCTTCTTGGATCGCTCATACATAAATATCTGTGAGTCAGAGAAGCAACCACCGACCCCAAGACCTCACCCCGAGCC    -  1

ATG GCT AGG CTC CTC ACC ACC TGC TGC CTG CTG CTC GCC CTG CTC GCC GCC TGC ACC GAC      60
Met Ala Arg Leu Leu Thr Thr Cys Cys Leu Leu Leu Ala Leu Leu Ala Ala Cys Thr Asp      20

GTC GCC CTC TCC AAG AAG GGC AAA GGC AGT CCC AGT GGT GGG GGT TGG GGC GCC GGG AGC     120
Val Ala Leu Ser Lys Lys Gly Lys Gly Ser Pro Ser Gly Gly Gly Trp Gly Ala Gly Ser      40

CAT CGC CAG CCC AGC TAC CCC CGC CAG CCG GGC TAC CCT CAT AAC CCA GGG TAC CCC CAT     180
His Arg Gln Pro Ser Tyr Pro Arg Gln Pro Gly Tyr Pro His Asn Pro Gly Tyr Pro His      60

AAC CCA GGG TAC CCC CAT AAC CCA GGT TAC CCA GGC TGG GGT CAA GGC TAC AAC CCA GGA     240
Asn Pro Gly Tyr Pro His Asn Pro Gly Tyr Pro Gly Trp Gly Gln Gly Tyr Asn Pro Gly      80

GGC TAC CCC CAT AAC CAC AAC CAG GGT GCT GTG GTG AAG CCA AAG CCC CCC AAA TGG CCA     300
Gly Tyr Pro His Asn His Asn Gln Gly Ala Val Val Lys Pro Lys Pro Pro Lys Trp Pro     100

GGA AGT TAC CAC AGC TAC TAC CAC TTC GAT AGA CCC GAT GAG TAC CGA TGG TGG AGT GCG     360
Gly Ser Tyr His Ser Tyr Tyr His Phe Asp Arg Pro Asp Glu Tyr Arg Trp Trp Ser Ala     120

GGG GCA GCA GCA GCG GGT GCT GTG GTG AAG CCA AAG CCC CCC AAA TGG CCA GGA AGT TAC     420
Gly Ala Ala Ala Ala Gly Leu Gly Leu Gly Tyr Ala Met Gly Arg Val             140

ATG TCA GGG ATG AAC TAC CAC TTC GAT AGA CCC GAT GAG TAC CGA TGG TGG AGT GAG AAC     480
Met Ser Gly Met Asn Tyr His Phe Asp Arg Pro Asp Glu Tyr Arg Trp Trp Ser Glu Asn     160

TCG CGT TAT CCC AAC CGG GTT TAC AGC GTT TAC TAC CGG GAT TAC CGG GAT TAC AGC CCA CCA CAG GAC     540
Ser Arg Tyr Pro Asn Arg Val Tyr Tyr Arg Asp Tyr Ser Ser Pro Val Pro Gln Asp     180
```

FIG. 2

```
GTC TTC GTG GCC GAT TGC TTT AAC ATC ACA GTG ACT GAG TAC AGC ATT GGC CCT GCT GCC    600
Val Phe Val Ala Asp Cys Phe Asn Ile Thr Val Thr Glu Tyr Ser Ile Gly Pro Ala Ala    200

AAG AAC ACC TCC GAG GCT GTG GCG GCA AAC ACG GAG GTG GAG ATG GAG AAC                660
Lys Lys Asn Thr Ser Glu Ala Val Ala Ala Asn Gln Thr Glu Val Glu Met Glu Asn        220

AAA GTG GTG ACG AAG GTG ATC CGC GAG ATG TGC GTG CAG CAG TAC CGC GAG TAC CGC CTG    720
Lys Val Val Thr Lys Val Ile Arg Glu Met Cys Val Gln Gln Tyr Arg Glu Tyr Arg Leu    240

GCC TCG GGC ATC CAG CTG CAC CTG CAC ACC TGG CTC GCC GTC CTC CTC CTC CTC CTC        780
Ala Ser Gly Ile Gln Leu His Pro Ala Asp Thr Trp Leu Ala Val Leu Leu Leu Leu Leu    260

ACC ACC CTT TTT GCC ATG CAC TGATGGGATGCCGTGCCCGGCCCTGTGGCAGTGAGATGACATCGTGTCCC     852
Thr Thr Leu Phe Ala Met His                                                        267

CGTGCCCACCCATGGGGTGTTCCTTGTCCTCGCTTTTGTCCATCTCTTTGGTGAAGATGTCCCCCGCTGCCTCCCCGCAG   931
GCTCTGATTTGGGCAAATGGGAGGGATTTGTCCTGTCCTGGTCGTTGGGCGTGGACGGCGTCGTGGTGGAGTGGGATG    1010
CCCAAAAAATGGCCTTCACCACTTCGAAATCTGAAATCCCAACCCTCTCTTTGCTAACAAGCAGGGTTTACCTAATCTG   1089
CCTGCAAGAGCGTATCTGAAATCTGAAATCCAACCCAAGCTGAGGTGCTTGGCAGCTCTTAATGTAGCTCTTTAATCTG   1168
GCGCCTTTCCCCAGGGCACACACCCTGGGCTACTGAGGTGCAATTGTGCAAAACACCTCTTAATCTGCCAATCCAACACG   1247
GGCGTCCCCAAGCAACACCCTGGGCTACTGAGGTGCAATTGTGCAAAACACCTCTTAATCTGCCAATCCAACACGTTTGG  1326
TAGGAACTGCCTCTGCTCAGCACTGCATTTTGCATGCTTGGGATTGGGCTCATCATATCATATCAGCAGCCCCCAAAAATA 1405
AGTGAGGCTGAAGCACCAGCACTGCCCAGAGGAAGGGGAGCGGCTACAGATCGCATCTCGCACAGATGCATCAACCACTG  1484
TGCCCTTTTATAGCCTGCCCAGAGGAAGGGGAGCGGCTACAGATCGCATCTCGCACAGATGCATCAACCACTGTGCCCTT  1563
ATGTATGATAGAGAACGAGTGCATCTCGCACAGATGCATCAACCACTGAGAGACTTGTTGCCATCAGCCCCAAAACCAAGG 1642
ATGCTAAATGCAGAACGGCCAAAGGGGAATCAGCCAGGAGGACTTGAATCAGCTCAACTGGATTGAATGGCAAAG       1721
GCATGAGTAGAACGAACGGCCAAGGGATGCTGCTGATGTATCATGTATGTGGGCACTGAATGCCACCCGTTGGCCATACC 1800
ATTGCTTCTGTGCTTCAGTTGCTTCAGTTGCTGATGTATCATGTAAGTTACACGTGTCAGTGTCTCG               1879
CACCGCGTAGAGCTAATATGTATCATGTATGTGGGCACTGAATGCCACCCGTTGGCCATACCCCAACCGTCCTAAACGATT 1958
TTCACGTCGCTGCTGTAACTTAAGTGAGATACACTTTCAGTATATTCAGCAAAAGGAATTC                     2017
```

FIG. 2 (cont.)

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: N-terminal ( x i ) SEQUENCE DESCRIPTION: SEQ ID NO:1:

| Lys | Lys | Gly | Lys | Gly | Lys | Pro | Ser | Gly | Gly | Gly | Glu | Gly |
|-----|-----|-----|-----|-----|-----|-----|-----|-----|-----|-----|-----|-----|
| 1   |     |     |     | 5   |     |     |     |     | 10  |     |     |     |

( 2 ) INFORMATION FOR SEQ ID NO:2:

( i ) SEQUENCE CHARACTERISTICS:
        ( A ) LENGTH: 2188 base pairs
        ( B ) TYPE: nucleic acid
        ( C ) STRANDEDNESS: double
        ( D ) TOPOLOGY: linear ( i i ) MOLECULE TYPE: cDNA to mRNA ( i x ) FEATURE:

( A ) NAME/KEY: CDS
( B ) LOCATION: 172..972

( x i ) SEQUENCE DESCRIPTION: SEQ ID NO:2:

```
GAATTCCCTC GGCAGCCAGC TCCTCCCTCT CGCTATTTAT TCCTTTCTCC CCCCCCTACG        60

CTGGATCTGG ATCATCTCAA GCCGAGCGGT GACGGCTTCT TGGATCGCTC ATACATAAAT       120

ATCTGTGAGT CAGAGGAAGC AACCACCGAC CCCAAGACCT CACCCCGAGC C ATG GCT        177
                                                        Met Ala
                                                         1

AGG CTC CTC ACC ACC TGC TGC CTG CTG GCC CTG CTG CTC GCC GCC TGC         225
Arg Leu Leu Thr Thr Cys Cys Leu Leu Ala Leu Leu Leu Ala Ala Cys
         5              10                  15

ACC GAC GTC GCC CTC TCC AAG AAG GGC AAA GGC AAA CCC AGT GGT GGG         273
Thr Asp Val Ala Leu Ser Lys Lys Gly Lys Gly Lys Pro Ser Gly Gly
     20              25                  30

GGT TGG GGC GCC GGG AGC CAT CGC CAG CCC AGC TAC CCC CGC CAG CCG         321
Gly Trp Gly Ala Gly Ser His Arg Gln Pro Ser Tyr Pro Arg Gln Pro
 35              40                  45                      50

GGC TAC CCT CAT AAC CCA GGG TAC CCC CAT AAC CCA GGG TAC CCC CAC         369
Gly Tyr Pro His Asn Pro Gly Tyr Pro His Asn Pro Gly Tyr Pro His
                 55                  60                  65

AAC CCT GGC TAT CCC CAT AAC CCC GGC TAC CCC CAG AAC CCT GGC TAC         417
Asn Pro Gly Tyr Pro His Asn Pro Gly Tyr Pro Gln Asn Pro Gly Tyr
         70                  75                  80

CCC CAT AAC CCA GGT TAC CCA GGC TGG GGT CAA GGC TAC AAC CCA TCC         465
Pro His Asn Pro Gly Tyr Pro Gly Trp Gly Gln Gly Tyr Asn Pro Ser
             85                  90                  95

AGC GGA GGA AGT TAC CAC AAC CAG AAG CCA TGG AAA CCC CCC AAA ACC         513
Ser Gly Gly Ser Tyr His Asn Gln Lys Pro Trp Lys Pro Pro Lys Thr
100                 105                 110

AAC TTC AAG CAC GTG GCG GGG GCA GCA GCG GCG GGT GCT GTG GTG GGG         561
Asn Phe Lys His Val Ala Gly Ala Ala Ala Ala Gly Ala Val Val Gly
115                 120                 125                 130

GGC TTG GGG GGC TAC GCC ATG GGG CGC GTT ATG TCA GGG ATG AAC TAC         609
Gly Leu Gly Gly Tyr Ala Met Gly Arg Val Met Ser Gly Met Asn Tyr
                135                 140                 145

CAC TTC GAT AGA CCC GAT GAG TAC CGA TGG TGG AGT GAG AAC TCG GCG         657
His Phe Asp Arg Pro Asp Glu Tyr Arg Trp Trp Ser Glu Asn Ser Ala
            150                 155                 160

CGT TAT CCC AAC CGG GTT TAC TAC CGG GAT TAC AGC AGC CCC GTG CCA         705
Arg Tyr Pro Asn Arg Val Tyr Tyr Arg Asp Tyr Ser Ser Pro Val Pro
        165                 170                 175

CAG GAC GTC TTC GTG GCC GAT TGC TTT AAC ATC ACA GTG ACT GAG TAC         753
Gln Asp Val Phe Val Ala Asp Cys Phe Asn Ile Thr Val Thr Glu Tyr
180                 185                 190

AGC ATT GGC CCT GCT GCC AAG AAG AAC ACC TCC GAG GCT GTG GCG GCA         801
Ser Ile Gly Pro Ala Ala Lys Lys Asn Thr Ser Glu Ala Val Ala Ala
195                 200                 205                 210

GCA AAC CAA ACG GAG GTG GAG ATG GAG AAC AAA GTG GTG ACG AAG GTG         849
Ala Asn Gln Thr Glu Val Glu Met Glu Asn Lys Val Val Thr Lys Val
                215                 220                 225

ATC CGC GAG ATG TGC GTG CAG CAG TAC CGC GAG TAC CGC CTG GCC TCG         897
Ile Arg Glu Met Cys Val Gln Gln Tyr Arg Glu Tyr Arg Leu Ala Ser
            230                 235                 240

GGC ATC CAG CTG CAC CCT GCT GAC ACC TGG CTC GCC GTC CTC CTC CTC         945
Gly Ile Gln Leu His Pro Ala Asp Thr Trp Leu Ala Val Leu Leu Leu
        245                 250                 255

CTC CTC ACC ACC CTT TTT GCC ATG CAC TGATGGGATG CCGTGCCCCG               992
Leu Leu Thr Thr Leu Phe Ala Met His
        260                 265

GCCCTGTGGC AGTGAGATGA CATCGTGTCC CCGTGCCCAC CCATGGGGTG TTCCTTGTCC      1052
```

```
TCGCTTTTGT  CCATCTTTGG  TGAAGATGTC  CCCCCGCTGC  CTCCCCGCAG  GCTCTGATTT      1112
GGGCAAATGG  GAGGGGATTT  TGTCCTGTCC  TGGTCGTGGC  AGGACGGCTG  CTGGTGGTGG      1172
AGTGGGATGC  CCAAAAAATG  GCCTTCACCA  CTTCCTCCTC  CTCTTCCTTT  CTGGGGCGGA      1232
GATATGGGCT  CGTCCAGCCC  TTATTGTCCC  TGCAAGAGCG  TATCTGAAAA  TCCTCTTTGC      1292
TAACAAGCAG  GGTTTTACCT  AATCTGCTTA  GCCCCAGTGA  CAGCAGAGCG  CCTTTCCCCA      1352
GGGCACACCA  ACCCCAAGCT  GAGGTGCTTG  GCAGCCACAC  GTCCCATGGA  GGCTGATGGG      1412
TTTTGGGGCG  TCCCAAGCAA  CACCCTGGGC  TACTGAGGTG  CAATTGTAGC  TCTTTAATCT      1472
GCCAATCCCA  ACCCTACCGT  GTAGATAGGA  ACTGCCTGCT  CTGCATTTTG  CATGCTGCAA      1532
ACACCTCCTG  CCGCAGCGCC  CCCAAAATAG  AGTGATTTGG  GAATAGTGAG  GCTGAAGCCA      1592
CAGCAGCTTG  GGATTGGGCT  CATCATATCA  ATCCATGATG  CTTTGCTTCC  AGCTGAGCCT      1652
CACTGCCCTT  TTATAGCCTG  CCCAGAGGAA  GGGAGCGCTG  CTAAATGCCC  AAAAAGGTAA      1712
CACTGAGCAA  AGCTTATTT   CAATGTATGA  TAGAGAACGA  GTGCATCTCG  CACAGATCAG      1772
CCATGGGAGC  ATCGTTTGCC  ATCAGCCCCA  AAACCCAAAG  GATGCTAAAA  TGCAGCCAAA      1832
GGGGAATCAA  GCACGCAGGG  AAGGACTTGA  ATCAGCTCAA  CTGGATTGAA  ATGGCAAAAG      1892
GCATGAGTAG  AACGAACGGC  AAGGGGATGC  TGGAGATCCA  CCTCCTGTGA  GCAAATTGTT      1952
CGATGCAGCC  AATGGAACTA  TTGCTTCTTG  TGCTTCAGTT  GCTGCTGATG  TGTACATAGG      2012
CTGTAGCATA  TGTAAAGTTA  CACGTGTCAA  GCTGCTCGCA  CCGCGTAGAG  CTAATATGTA      2072
TCATGTATGT  GGGCACTGAA  TGCCACCGTT  GGCCATACCC  AACCGTCCTA  AACGATTTTC      2132
ACGTCGCTGT  AACTTAAGTG  GAGATACACT  TTCAGTATAT  TCAGCAAAAG  GAATTC         2188
```

( 2 ) INFORMATION FOR SEQ ID NO:3:

( i ) SEQUENCE CHARACTERISTICS:
        ( A ) LENGTH: 267 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Met  Ala  Arg  Leu  Leu  Thr  Thr  Cys  Cys  Leu  Leu  Ala  Leu  Leu  Leu  Ala
 1              5                        10                       15

Ala  Cys  Thr  Asp  Val  Ala  Leu  Ser  Lys  Lys  Gly  Lys  Gly  Lys  Pro  Ser
               20                       25                       30

Gly  Gly  Gly  Trp  Gly  Ala  Gly  Ser  His  Arg  Gln  Pro  Ser  Tyr  Pro  Arg
          35                       40                       45

Gln  Pro  Gly  Tyr  Pro  His  Asn  Pro  Gly  Tyr  Pro  His  Asn  Pro  Gly  Tyr
     50                       55                       60

Pro  His  Asn  Pro  Gly  Tyr  Pro  His  Asn  Pro  Gly  Tyr  Pro  Gln  Asn  Pro
65                       70                       75                       80

Gly  Tyr  Pro  His  Asn  Pro  Gly  Tyr  Pro  Gly  Trp  Gly  Gln  Gly  Tyr  Asn
                    85                       90                       95

Pro  Ser  Ser  Gly  Gly  Ser  Tyr  His  Asn  Gln  Lys  Pro  Trp  Lys  Pro  Pro
               100                      105                      110

Lys  Thr  Asn  Phe  Lys  His  Val  Ala  Gly  Ala  Ala  Ala  Gly  Ala  Val
          115                      120                      125       Val

Val  Gly  Gly  Leu  Gly  Gly  Tyr  Ala  Met  Gly  Arg  Val  Met  Ser  Gly  Met
     130                      135                      140

Asn  Tyr  His  Phe  Asp  Arg  Pro  Asp  Glu  Tyr  Arg  Trp  Trp  Ser  Glu  Asn
145                      150                      155                      160

Ser  Ala  Arg  Tyr  Pro  Asn  Arg  Val  Tyr  Tyr  Arg  Asp  Tyr  Ser  Ser  Pro
```

```
                165                          170                          175
Val  Pro  Gln  Asp  Val  Phe  Val  Ala  Asp  Cys  Phe  Asn  Ile  Thr  Val  Thr
               180                      185                     190

Glu  Tyr  Ser  Ile  Gly  Pro  Ala  Ala  Lys  Lys  Asn  Thr  Ser  Glu  Ala  Val
          195                      200                     205

Ala  Ala  Ala  Asn  Gln  Thr  Glu  Val  Glu  Met  Glu  Asn  Lys  Val  Val  Thr
     210                      215                     220

Lys  Val  Ile  Arg  Glu  Met  Cys  Val  Gln  Gln  Tyr  Arg  Glu  Tyr  Arg  Leu
225                      230                     235                          240

Ala  Ser  Gly  Ile  Gln  Leu  His  Pro  Ala  Asp  Thr  Trp  Leu  Ala  Val  Leu
               245                      250                     255

Leu  Leu  Leu  Leu  Thr  Thr  Leu  Phe  Ala  Met  His
               260                      265
```

( 2 ) INFORMATION FOR SEQ ID NO:4:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( i x ) FEATURE:
        ( A ) NAME/KEY: modifiedbase
        ( B ) LOCATION: 14
        ( D ) OTHER INFORMATION: /modbase=i ( i x ) FEATURE:
        ( A ) NAME/KEY: modifiedbase
        ( B ) LOCATION: 17
        ( D ) OTHER INFORMATION: /modbase=i ( i x ) FEATURE:
        ( A ) NAME/KEY: modifiedbase
        ( B ) LOCATION: 20

( x i ) SEQUENCE DESCRIPTION: SEQ ID NO:4:

GCGGAATTCG AAAAAAAGGA AARGGNAA        28

( 2 ) INFORMATION FOR SEQ ID NO:5:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: YES ( i x ) FEATURE:
        ( A ) NAME/KEY: modifiedbase
        ( B ) LOCATION: 14
        ( D ) OTHER INFORMATION: /modbase=i ( i x ) FEATURE:
        ( A ) NAME/KEY: modifiedbase
        ( B ) LOCATION: 17
        ( D ) OTHER INFORMATION: /modbase=i ( x i ) SEQUENCE DESCRIPTION: SEQ ID NO:5:

GGCGAATTCA TGGATAASWN GG        22

( 2 ) INFORMATION FOR SEQ ID NO:6:

( i ) SEQUENCE CHARACTERISTICS:

-continued

```
           ( A ) LENGTH: 31 base pairs
           ( B ) TYPE: nucleic acid
           ( C ) STRANDEDNESS: single
           ( D ) TOPOLOGY: linear ( i i i ) HYPOTHETICAL: NO ( i v ) ANTI-SENSE: NO ( i x ) FEATURE:
           ( A ) NAME/KEY: modifiedbase
           ( B ) LOCATION: 14
           ( D ) OTHER INFORMATION: /modbase=i ( i x ) FEATURE:
           ( A ) NAME/KEY: modifiedbase
           ( B ) LOCATION: 17
           ( D ) OTHER INFORMATION: /modbase=i ( i x ) FEATURE:
           ( A ) NAME/KEY: modifiedbase
           ( B ) LOCATION: 20
           ( D ) OTHER INFORMATION: /modbase=i ( x i ) SEQUENCE DESCRIPTION: SEQ ID NO:6:

GCGGAATTCG AAAAAAAGGA AARGGNAARC C                                          31

( 2 ) INFORMATION FOR SEQ ID NO:7:

( i ) SEQUENCE CHARACTERISTICS:
           ( A ) LENGTH: 25 base pairs
           ( B ) TYPE: nucleic acid
           ( C ) STRANDEDNESS: single
           ( D ) TOPOLOGY: linear ( i i i ) HYPOTHETICAL: NO ( i v ) ANTI-SENSE: YES ( i x ) FEATURE:
           ( A ) NAME/KEY: modifiedbase
           ( B ) LOCATION: 14
           ( D ) OTHER INFORMATION: /modbase=i ( i x ) FEATURE:
           ( A ) NAME/KEY: modifiedbase
           ( B ) LOCATION: 17
           ( D ) OTHER INFORMATION: /modbase=i ( x i ) SEQUENCE DESCRIPTION: SEQ ID NO:7:

GGCGAATTCA TGGATAASWN GGYTG                                                 25

( 2 ) INFORMATION FOR SEQ ID NO:8:

( i ) SEQUENCE CHARACTERISTICS:
           ( A ) LENGTH: 34 base pairs
           ( B ) TYPE: nucleic acid
           ( C ) STRANDEDNESS: single
           ( D ) TOPOLOGY: linear ( i i i ) HYPOTHETICAL: NO ( i v ) ANTI-SENSE: YES ( x i ) SEQUENCE DESCRIPTION: SEQ ID NO:8:

GCGATGGCTC CCGGCGCCCC AACCCCCACC ACTG                                       34
```

DNA ENCODING A PROTEIN WHICH COPURIFIES WITH ACETYLCHOLINE RECEPTOR INDUCING ACTIVITY AND USES THEREFOR

FUNDING

Work described herein was funded by the National Institutes of Health, the McKnight Foundation and the James S. McDonnell Foundation.

BACKGROUND

Acetylcholine is the chemical mediator at all synapses between preganglionic and postganglionic fibers of the autonomic nervous systems, which has an important effect on control of smooth muscle and controls many internal functions. Acetylcholine is also a chemical mediator at all myoneural junctions, all postganglionic parasympathetic and some postganglionic sympathetic endings. Acetylcholine molecules are released into the synaptic cleft by a mechanism which is not fully understood and, once released, diffuse across the cleft and combine with receptor molecules (acetylcholine receptors or AChRs) present in the postsynaptic neuron membrane or muscle cell membrane. At the neuromuscular junction, as at other chemical synapses, the number and distribution of neurotransmitter receptors is a critical factor in determining the response to presynaptic stimulation.

A key event in the formulation of the neuromuscular junction is the accumulation of acetylcholine receptors in the muscle membrane opposed to the nerve terminal. It is known that at the mature neuromuscular junction, AChRs are packed in the postsynaptic membrane and highly localized. That is, receptors are present in the postsynaptic membrane at a density in excess of $10,000/\mu m^2$ and more than 70% of the receptors are restricted to the endplate, which comprises less than 0.1% of the muscle surface membrane. Little is known about how AChRs are inserted into and localized within the neuromuscular junction.

SUMMARY OF THE INVENTION

The present invention relates to isolated DNA encoding a protein which appears at an early stage in spinal cord development, is concentrated in motor neurons and appears to have a role in neuromuscular junction formation. It further relates to RNA transcribed from the isolated DNA and the encoded protein itself, referred to as acetylcholine receptor-inducing activity (ARIA), which promotes the synthesis and accumulation of acetylcholine receptors in muscle cells. The glycoprotein has been purified on the basis of its ability to increase the rate of insertion of AChRs into the surface membrane of a skeletal muscle fiber during a developmental stage (i.e., the surface membrane of myotubes). Specifically, a glycoprotein has been isolated from chick brain on the basis of its ability to increase the rate of insertion of AChRs into the surface membrane of cultured chick myotubes. The glycoprotein has been shown to promote the synthesis of AChRs, probably by enhancing transcription of the gene which encodes the AChRs α subunit. ARIA has also been shown to increase AChR levels in mammalian muscle.

ARIA co-purifies with a protein that migrates as a broad band centered at $M_r 42,000$ in SDS gels. Oligonucleotides whose sequences correspond to portions of the chemically determined sequence of the protein present in the SDS gel band in which ARIA was concentrated have been used to amplify from chicken brain cDNA a 34-nucleotide sequence encoding 11 amino acids of ARIA. A corresponding synthetic 34-mer was used to screen an E18 chick brain cDNA library and the insert of one positive clone has been sequence in its entirety (Seq. ID #2). The protein obtained from chick brain in this manner has been characterized and shown to exhibit considerable homology to the mammalian prion protein. Thus, it is referred to an chick prion-like protein (chick PLP). The prion-like protein has been shown to include a typical signal peptide, a series of eight imperfect hexapeptide repeats in the N-terminal half of the molecule in which every third residue is proline and every sixth residue is glycine, an uninterrupted stretch of 20 nonpolar amino acids flanked by charged residues near the middle of the molecule and a shorter hydrophobic region at the C-terminus. A portion of the chick prion-like protein appears to be anchored to the surface membrane via a glycosyl-phosphatidylinositol anchor.

The present invention also relates to an appropriate host cell, such as neuroblastoma cells, transfected with cDNA encoding prion-like protein, which express recombinant prion-like protein. It further relates to material released into the medium from the transfected cells after they are exposed to an enzyme, such as bacterial phosphoinositol specific phospholipase C and to material of slightly lower molecular weight present in medium conditioned by transfected cells in the absence of added enzyme. These appear to represent, respectively, an insoluble form of prion-like protein, which includes a hydrophobic transmembrane region, and a soluble form of prion-like protein.

The present invention also relates to reagents, which can be oligonucleotides or antibodies, useful in the method of the present invention of identifying similar prion-like proteins or DNA or RNA encoding similar prion-like proteins in other chick tissues and in tissues from other animals, including humans. The present invention further relates to a method of identifying or designing small ligands which cross the blood-brain barrier.

Oligonucleotide probes whose sequences are derived from the sequence of the isolated cDNA (Seq. ID #2) can be used to identify genes encoding similar proteins in mammalian cells. Alternatively, similar proteins in mammalian cells can be identified using antibodies, particularly monoclonal antibodies, reactive with ARIA.

As a result of the work described herein, a glycoprotein which promotes synthesis and accumulation of acetylcholine receptors is available, as are DNA encoding the glycoprotein and a method of producing prion-like protein or an active fragment thereof. The protein has been produced in both an insoluble and a soluble form. The protein can be used to enhance receptor synthesis, accumulation and survival at neuromuscular junctions. The protein itself (or an active portion thereof) can be used for this purpose. It can be delivered using known means, such as through the use of a minipump. Alternatively, DNA encoding the prion-like protein or an active prion-like protein portion can be incorporated into an appropriate expression system, such as a retroviral vector, and expressed, resulting in production of the protein and enhanced AChRs synthesis and accumulation in individuals in whom neurotransmitter receptor number and/or function, and, thus, nerve or muscular function, is compromised. This will be useful in treating conditions and diseases in which there is a deficit of neural transmitter receptors. For example, it will be useful in treating degenerative neurological disorders (e.g., Alzheimer's Disease and any conditions which are characterized by a deficit of AChRs), dementias associated with other chronic diseases (e.g., Huntington's Disease, Parkinson's Disease) and diseases of the peripheral nervous system in which there is a deficit of AChRs (e.g, myasthenia gravis).

BRIEF DESCRIPTION OF THE DRAWINGS

FIG. 1A: Left lane, starting material is fraction 17 from the C4 column; lanes 1-6, aliquots of eluted proteins were analyzed by SDS-PAGE.

FIG. 1B: Remainder of each sample was assayed for AChR inducing activity.

FIG. 2 is the nucleotide sequence (Seq. ID #2) and the deduced amino acid sequence (Seq. ID #3) of the 2.2 kb insert from a positive clone obtained by screening an E18 chick brain cDNA library in lambda gt10 and introduced into a plasmid designated p65-21.

FIG. 3A shows results of Northern blot analysis of chick-PLP in spinal cord and brain at the indicated stages. FIG. 3B shows the tissue distribution of chick-PLP mRNA in E17 and adult animals. SC = spinal cord; Giz = gizzard; Liv = liver; Lu = lung; Int = intestine.

DETAILED DESCRIPTION OF THE INVENTION

Although nerve-derived polypeptides which might mediate crucial processes in accumulation of AChRs at developing neuromuscular junctions have been identified, it was not known, until the work described herein, if any of these putative trophic factors act at developing or mature neuromuscular junctions.

As described herein, a protein has now been isolated (purified) from chick brain on the basis of its ability to promote the synthesis and accumulation of AChRs in cultured muscle cells. As also described herein, cDNA encoding the major sequenceable protein in purified preparations of this acetylcholine receptor inducing activity (ARIA) has been isolated. The protein encoded by the cDNA has been shown to have significant homology to the mammalian prion protein and is referred to as chick prion-like protein. Chick prion-like protein is expressed in the spinal cord and brain early in embryonic development and, in the spinal cord, appears to be concentrated in motor neurons. Preliminary assessment of the distribution of the protein demonstrated that it is highly concentrated in nerves that make acetyl choline. Thus, it is potentially useful as an agent or a drug to enhance AChR synthesis and accumulation in individuals in which synthesis and accumulation are compromised.

The following is a description of work which led to purification of ARIA, isolation of cDNA encoding chick prion-like protein and characterization of both.

Purification of ARIA

Figure 1A:
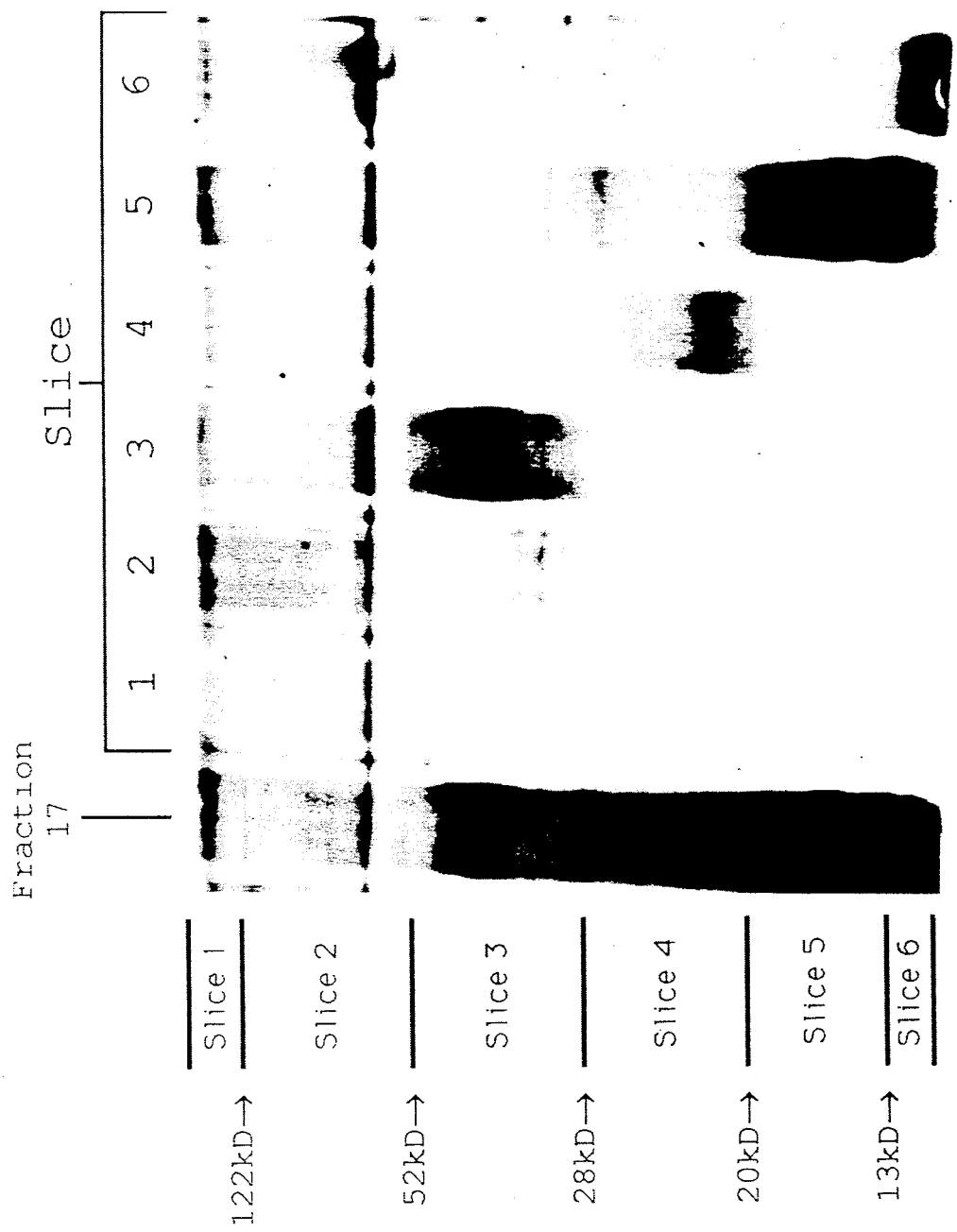
FIGS. 1A-1B shows the results of a bioassay of material eluted from slices of an SDS polyacrylamide gel loaded with one of the active fractions from the fifth step of the seven step purification protocol described in Ordinate:[125] BgTx binding sites per culture well. ARIA concentration is expressed as μl of starting (C4) material assuming 100% recovery at each stage. Exposure to SDS and electrophoresis reduced activity 5-10 fold compared to control (dotted line). Bars = standard deviations; N = 4.
Figure 1B:
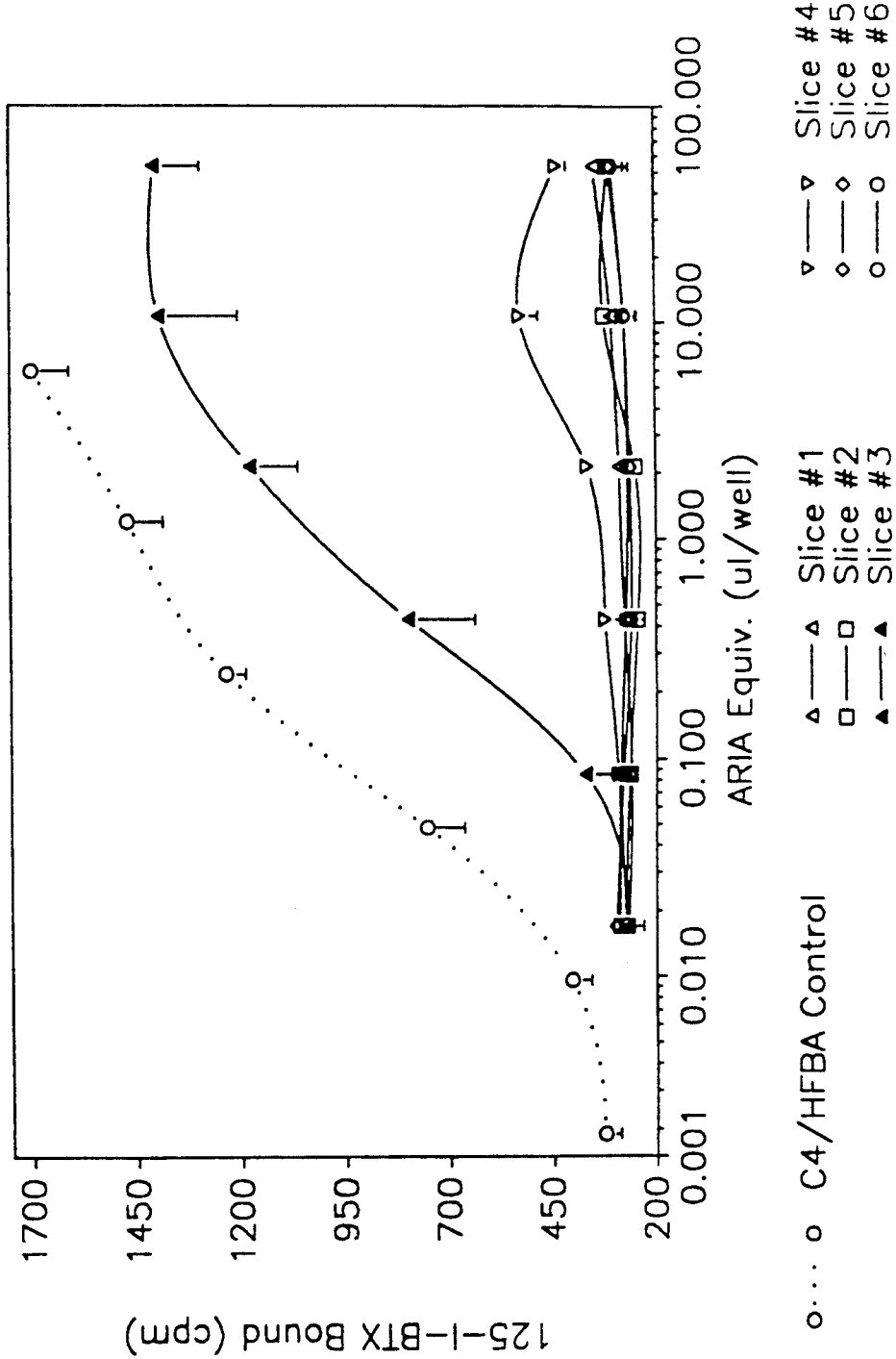

Acetylcholine receptor inducing activity (ARIA) co-purifies, through a number of chromatographic steps, with a protein that migrates as a broad band centered at Mr 42,000 in SDS gels. Usdin, T.B., and Fischbach, G.D., *J. Cell Biol.*, 103:493 (1986). FIG. 1 shows a bioassay of material eluted from slices of a gel loaded with one of the active fractions from the fifth step of a seven step purification protocol, a C4 reverse phase column. The purification protocol is described in Example 1. The boundaries of each segment and the relative mobility of each boundary are indicated to the left in FIG. 1A. The left lane contained starting material which was fraction 17 from the C4 column. Aliquots of eluted proteins were analyzed by SDS-PAGE (FIG. 1, lanes 1-6). The remainder of each sample was assayed for AChR inducing activity. (See Example 2) ARIA was concentrated in the third gel slice (which contained the broad, silver stained band).

Isolation and Characterization of cDNA Encoding ARIA

A single N-terminal amino acid sequence of 13 residues (KKGKGKPSGGGEG; Seq ID #1) was obtained when the band in which ARIA was concentrated was electroblotted onto an Immobilon membrane and analyzed by automated Edman degradation. The same sequence, with the exception of residue 12, plus 13 additional amino acids was obtained following further purification of the band by size exclusion HPLC. The same initial sequence (amino acids 25-58 of Seq. ID #3) was obtained following the final step in the protocol, analytical reverse phase chromatography on a C18 column. Little or no silver stained protein other than the 42 kD band was evident in SDS gels following the last two procedures.

Pairs of degenerate oligonucleotide primers that correspond to amino acids 1-7 and 19-23 of the chemically determined sequence (amino acids 25-58 of Seq. ID #3) were used in the polymerase chain reaction to amplify from chicken brain cDNA a 34-nucleotide sequence that corresponds to the 3' nucleotide of the 7th amino acid codon through the 3' nucleotide of the 18th amino acid codon (nucleotides 264-297 of Seq. ID #2). Cathala, G., et al., DNA, 2:329 (1983); Sambrook, J., et al., *Molecular Cloning: A Laboratory Manual*, 2nd Edition (Cold Spring Harbor Laboratory Press, 1989). (See Example 3)

A synthetic 34-mer with the same sequence was then used to screen 250,000 phage from an E18 chick brain cDNA library in lambda gt10 (kindly provided by D. Fambrough). (See Example 4) Four positive clones were obtained, three with 2.2 kb inserts and one with a 1.9 kb insert. Restriction maps and sequence analysis revealed that all three 2.2 kb clones were identical, and that the 1.9 kb clone shared the same 3' end but was truncated by 300 nucleotides at its 5' end.

One of the 2.2 kb inserts (in a plasmid designated p65-21) was sequenced in its entirety. The nucleotide sequence of the 2.2 kb insert of plasmid p65-21 is shown in FIG. 2 (Seq. ID #2). The nucleotide sequence was determined on both strands by the dideoxy chain termination method using synthetic oligonucleotide primers and either Sequenase (U.S. Biochemicals) or Taq polymerase (Promega). The cDNA predicts a protein of 267 amino acids (Seq. ID #3). The presumed initiator methionine (shaded in FIG. 2) is not preceded by an in-frame stop codon, but it occurs in a favorable context for translation initiation. Kozak, M., *J. Mol. Biol.*, 196:947 (1987). Moreover, this methionine begins a typical signal peptide sequence, whose predicted cleavage site between residues $ser^{24}$ and $lys^{25}$ is followed by the N-terminal amino acid sequence determined by Edman degradation (amino acids 25-58 of Seq. ID #3). Von Heijne, G., *J. Mol. Biol.*, 184:99 (1985); Foltz, R.J., and Gordon, J.I., *Biochem. Biophys. Res. Comm.*, 146:870 (1987). Thus, there can be no doubt that the p65-21 insert encodes the partially sequenced protein. There is a 5' untranslated region of 171 nucleotides and a 3' untranslated region of 1216 nucleotides that does not include a poly(A) tail or a polyadenylation signal.

In addition to the signal peptide, several other structural features of the predicted amino acid sequence are notable (FIG. 2; Seq. ID #3). There is a series of eight imperfect hexapeptide repeats ($arg^{42}$-$pro^{89}$) in the N-terminal half of the molecule in which every third residue is proline and every sixth residue is glycine. These are doubly underlined in FIG. 2. An uninterrupted stretch of 20 nonpolar amino acids ($val^{119}$-$gly^{138}$) flanked by charged residues is located near the middle of the molecule, and there is a shorter hydrophobic region at the C-terminus ($trp^{252}$-$met^{266}$). The two hydrophobic regions are singly underlined. There are three potential asparagine-linked glycosylation sites in the molecule (asn residues 188, 203, 212). They are shaded in FIG. 2. A fourth asparagine residue (#96) is separated from a serine residue by proline, and therefore is unlikely to be utilized as a glycosylation site. Bause, E., *Biochem. J.*, 209:331 (1983). N-glycanase (Genzyme) digestion experiments indicate that at least some of the sites are, in fact, glycosylated. The sequence also contains two cysteine residues (residues 186, 231, shaded in FIG. 2) that provide the potential for intramolecular disulfide bond formation.

Computer searches of protein data bases revealed that the predicted protein is homologous to the mammalian prion protein (PrpC). Oesch, B., et al., *Cell*, 40:735 (1985); Basler, K., et al., *Cell*, 46:417 (1986); Prusiner, S.B., *Annu. Rev. Microbiol.*, 43:345 (1989). Therefore, the p65-21 insert encoded protein is referred to as the chick prion-like protein (ch-PLP). With 1 gap in the ch-PLP sequence and 5 gaps in the mouse prion protein sequence, the two are identical at 33% of the amino acid positions. The degree of similarity rises to 43% if conservative substitutions are taken into account. An uninterrupted stretch of 24 amino acids (ch-PLP residues $pro^{112}$-$tyr^{135}$), that includes 17 of the 20 nonpolar residues in the central region, is identical in the chick and mouse proteins. One of the two cysteine residues in the mammalian PrPc (residue 178) occurs in the same position (after alignment) as one of the cysteines in the ch-PLP and the other (PrP $cys^{213}$) is displaced by one 4 residues. The two predicted N-linked glycosylation sites in the prion protein (residues 180, 196) occur at positions close to two of the three sites in ch-PLP (residues 188, 203).

The mammalian prion protein also displays the same structural domains as the ch-PLP, including similar glycine- and proline-rich repeats in the N-terminal half of the molecule as well as central and C-terminal hydrophobic regions. Oesch, B. et al., *Cell*, 40:735 (1985); Basler, K., et al., *Cell*, 46:417 (1986); Prusiner, S.B., *Annu. Rev. Microbiol.*, 43:345 (1989); Westaway, D., et al., *Cell*, 51:651 (1987). Further, like PrPC, a fraction of the ch-PLP molecules appear to be anchored to the surface membrane via a glycosyl-phosphatidylinositol anchor. Stahl, N., et al., *Cell*, 51:229 (1987); Stahl, N., et al., *Biochem.*, 29:5405 (1990).

Neuroblastoma N2a cells transfected with the cDNA insert express recombinant ch-PLP, and immunoreactive material is release into the medium after the cells are exposed to bacterial phosphoinositol specific phospholiphase C. Material of slightly lower molecular weight appeared in medium conditioned by transfected cells in the absence of added enzyme. Soluble forms of PrPC have also been reported. Caughey, B., et al., *Proc. Natl. Acad. Sci. USA*, 85:4657 (1988); Borchelt, D.R., et al., *Cell Biol.*, 110:743 (1990).

Figure 3B:
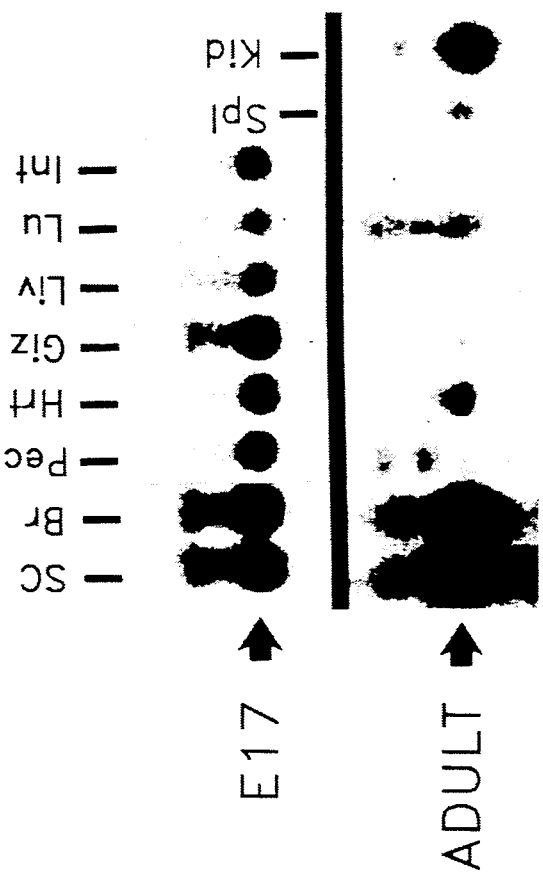
FIGS. 3A-3B shows the results of Northern blot analysis of chick-PLP.
Figure 3A:
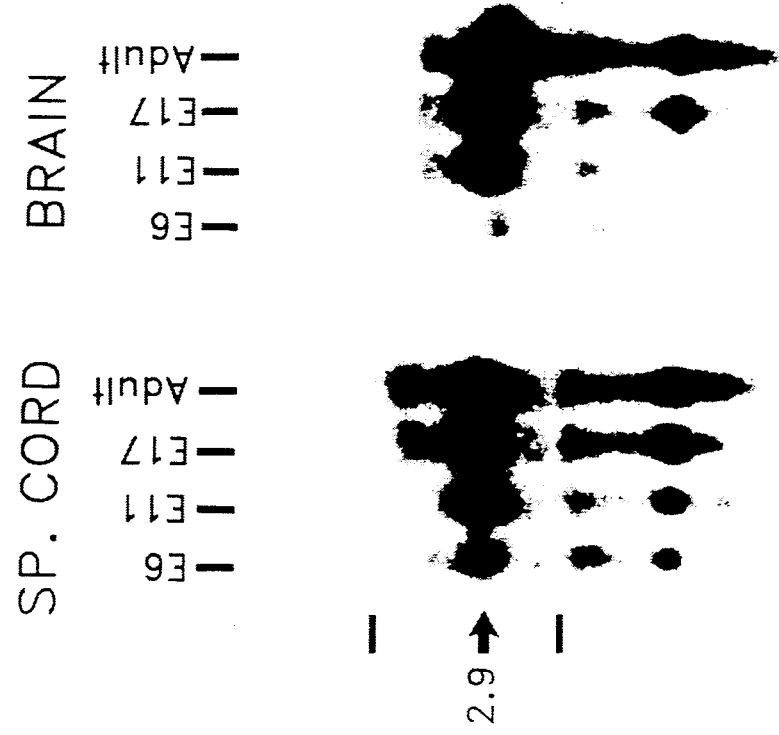

Northern blot analysis was carried out of chick-PLP in spinal cord and brain at various stages, as described in Example 5. Results are shown in FIGS. 3A and 3B. The major chick mRNA detected on Northern blots probed with the p65-21 insert is 2.9 kb (See FIG. 3A). It is significant that this mRNA is evident in E6 spinal cords because about this time motor axons are in the process of forming functional contacts in the periphery and the first muscle cell AChR clusters appear surrounding the nerve trunk. Landmesser L., and Morris, D., *J. Physiol.*, 249:301 (1975); Morgan, M., University Microfilms, Washington University, PhD Thesis (1990). The amount of the spinal cord 2.9 kb message increases during subsequent embryonic development, reaching highest levels in the adult chicken. The same time course of gene expression was observed in the brain (FIG. 3A), the source of the purified protein. Small amounts of a 3.5 kb MRNA are also apparent in both spinal cord and brain, especially in poly (A)+ mRNA. The significance and origin of the larger mRNA remain to be determined. A band of about 1 kb varied from preparation to preparation, and probably represents a degradation product. It is noteworthy that the mammalian PrP gene contains a single coding exon, and only one mRNA band has been detected on Northern blots. Oesch, B., et al., *Cell*, 40:735 (1985); Basler, K., et al., *Cell*, 46:417 (1986); Prusiner, S.B., *Annu. Rev. Microbiol.*, 43:345 (1989).

Figure 4:
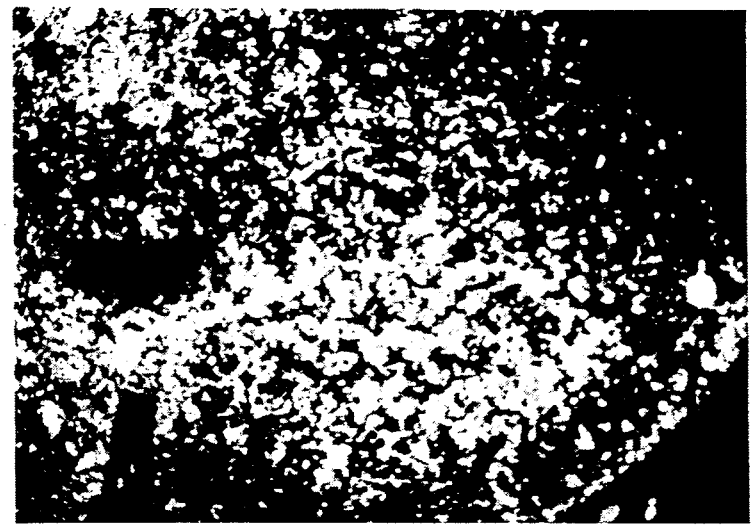
FIG. 4 is a darkfield micrograph of a section of lumber spinal cord from an adult chicken hybridized in situ with a $^{35}$S-labeled anti-sense probe for chick-PLP mRNA.

In adult chickens, the 2.9 kb MRNA is highly concentrated in the CNS, with significant levels evident only in the kidney among the non-neural tissues surveyed (FIG. 3B). In E17 embryos the 2.9 kb mRNA is most concentrated in the CNS, although relatively larger amounts are evident in several non-neural tissues (FIG. 3B). In situ hybridization of sections from adult spinal cord was carried out, as described in Example 5, using a $^{35}$S-labeled anti-sense probe for chick-PLP mRNA. Results showed that the mRNA is concentrated in the ventral horn (FIG. 4). Label above the sense strand control is evident throughout the cord, but clusters of grains, presumably over motor neurons, are particularly evident in the ventral gray matter.

Figure 5:
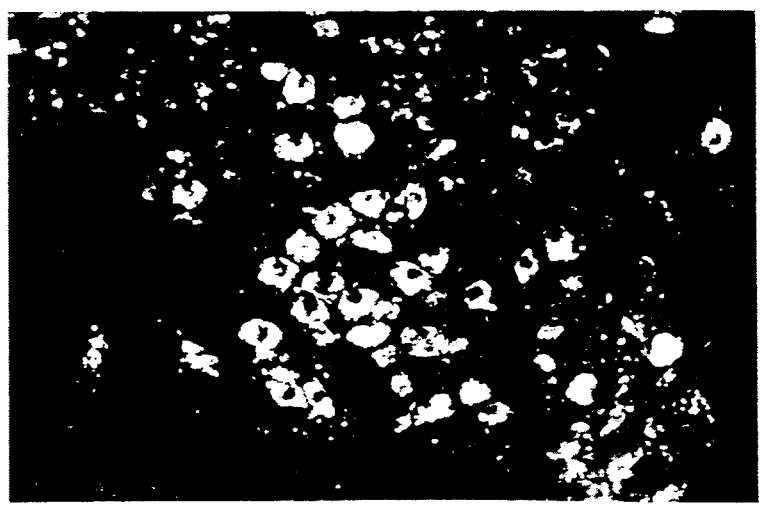
FIG. 5 is a fluorescence micrograph of a section of lumbar spinal cord from an E18 chicken stained with a monoclonal antibody directed against a specific peptide corresponding to residues lys[25] to gly[35] of chick-PLP. Dorsal to the top; lateral to the right.

Immunohistochemical experiments indicate that the protein is concentrated in the ventral horn. A section of lumbar spinal cord from an E18 chicken was stained with antibodies directed against a synthetic peptide corresponding to residues lys[25] to gly[35] of the ch-PLP, as described in Example 6. FIG. 5 is a fluorescence micrograph of such a section. The staining was markedly reduced when the antibodies were preincubated with excess peptide. Label, above background, was observed in the dorsal horn, but it was less intense than that present in motor neurons.

Elucidation of the relationship between the ch-PLP and the 42 kb ARIA is continuing. Indirect evidence suggests that they are identical or closely related. For example, ARIA and the ch-PLP remain associated throughout a series of chromatographic steps that result in a $10^6$ fold purification of the AChR inducing activity. Further, the ch-PLP and the AChR inducing activity shift to lower molecular weight following digestion of purified preparations with N-glycanase. Finally the ch-PLP and its mRNA are concentrated in motor neurons, consistent with the hypothesis that this protein is involved in neuromuscular junction formation and maintenance.

APPLICATIONS OF THE PRESENT INVENTION

The present invention makes available purified protein and cDNA encoding the protein, which appears to have a role in neuromuscular junction formation and has been shown to promote the synthesis and accumulation of acetylcholine receptors in muscle cells. This has been accomplished, as described herein, by isolating acetylcholine receptor inducing activity from chick brain; designing oligonucleotide primers based on the single N-terminal amino acid sequence (amino acids 25-58 of Seq. ID #3) obtained from sequence analysis of ARIA; amplifying from chicken brain cDNA a longer oligonucleotide probe by means of PCR using the oligonucleotide primers; identifying positive cDNA clones by means of the longer oligonucleotide probe; and expressing the recombinant protein in neuroblastoma cells transfected with a cDNA insert obtained from clones identified in this manner.

Thus, purified ARIA and recombinant chick prion-like protein are available. The recombinant chick prion-like protein has been produced by preparing an expression vector which expresses DNA encoding chick prion-like protein in an appropriate host cell; introducing the expression vector into the host cell, using known techniques, to produce a recombinant host cell in which the protein encoded by the DNA in the expression vector is expressed; maintaining the recombinant host cell under conditions appropriate for expression of the encoded protein, to produce recombinant chick prion-like protein; and recovering the chick prion-like protein. The protein can be recovered using known techniques, such as recovery using an antibody or other reagent which specifically binds the protein.

The protein produced in this manner can be used to produce antibodies, both polyclonal and monoclonal, which can, in turn, be used to identify chick prion-like protein equivalents (proteins cross-reactive with chick prion-like protein) in other animals and other tissues.

The oligonucleotide primers and probes described in the examples, as well as other oligonucleotides designed on the basis of DNA encoding chick prion-like protein, can be used, in known methods, to identify DNA (or RNA) encoding proteins similar to chick prion-line protein in other animals and other tissues.

Thus, the term chick prion-like protein, as used herein, includes proteins and polypeptides which: 1) have a) the same amino acid sequence (Seq. ID #3) as chick prion-like protein or a substantially similar amino acid sequence; b) are encoded by an oligonucleotide sequence the same as or substantially similar to that encoding chick prion-like protein as described (See FIG. 2); or c) are recognized by an antibody which binds the chick prion-like protein purified or produced as described herein and 2) have acetylcholine receptor inducing activity. A substantially similar amino acid sequence is one which differs from the chick prion-like protein sequence (e.g., the sequence of FIG. 2 Seq. ID #3) but the resulting polypeptide or protein has substantially the same function (acetylcholine receptor inducing activity) as chick prion-like protein. A substantially similar nucleic acid sequence is one which differs from the chick prion-like protein-encoding sequence (e.g., the sequence of FIG. 2 Seq. ID #2), but encodes a product having substantially the same function as chick prion-like protein.

The present invention also has clinical or diagnostic applications. For example, it is possible to enhance AChR production and survival. This can be done, for example, by introducing an oligonucleotide sequence encoding all or an active portion of the chick prion-like protein or of an ARIA of other (non-chick) origin into an individual in an appropriate expression vector (e.g., a retroviral vector). Expression of the encoded protein makes available enhanced quantities of ARIA and, thus, promotes AChR synthesis and/or accumulation. Alternatively, the protein itself or a fragment thereof can be used, as can a small ligand isolated or designed on the basis of a comparison with the chick prion-like protein. As a result, it is possible to use materials described herein to treat degenerative neurological disorders, such as Alzheimer'Disease or any condition that results in degeneration and/or loss in number/function of AChRs or deficits of other neurotransmitter receptors. Dementias associated with other chronic diseases, such as Huntington's Disease and Parkinson's Disease, can also be treated (prevented an/or reduced in severity) by providing the protein. It is also possible to treat diseases of the peripheral nervous system by administering the protein of the present invention. It is also possible to use antibodies specific for ARIA or chick prion-like protein and oligonucleotide sequences described herein for diagnostic purposes. That is, they can be used to assess the adequacy of this or a corresponding protein associated with AChR synthesis and accumulation and, thus, an individual's ability to produce and maintain adequate AChR levels.

The invention is illustrated by the following examples, which are not intended to be limiting in any way.

EXAMPLE 1

Purification of a 42-KD ARIA

Purification of a 42 kD ARIA was carried out by the following seven-step procedure: (1) delipidation of 1000 chicken brains by acetone and ether extraction; (2) extraction of the residual brain "mud" with a cocktail containing trifluoroacetic acid (TFA), formic acid, hydrochloric acid, sodium chloride, and several protease inhibitors followed by adsorption onto Vydac C18 and batch elution with acetronile to desalt and further defat;

(3) ion-exchange chromatography on CM Sepharose eluted with a linear salt gradient; (4) reverse-phase (RP) chromatography on a semipreparative Vydac C4 column eluted with a gradient of isopropyl alcohol (IPA) in TFA; (5) RP chromatography on the semipreparative Vydac C4 eluted with a gradient of IPA in heptafluorobutyric (HFBA); (6) size-exclusion chromatography of a TSK3000SW column; and (7) analytical RP chromatography on a microbore Vydac C18 column eluted with a gradient of acetonitrile in TFA.

To minimize losses, it is often useful to begin with ARIA purified through step 5 (referred to as C4/HFBa fractions). Receptor-inducing activity elutes from this C4 column as a symmetric, broad peak just before the main protein peak. FIG. 1A shows a typical elution in which each fraction was assayed at three doses (FIG. 1, middle). In silver-stained gels of the same fractions, a descending staircase of broad bands ranging between M, 45,000 and M, 35,000 was evident in the successive active fractions through fraction 18. The same pattern has been observed in C4/HFBA bioactive fractions from more than 20 different extractions. After digesting active fractions with N-glycanase (Genzyme; peptide:N-glycosidase F), an enzyme that cleaves asparagine-linked glycans, all of the bands migrate at the same rate (~M, 33,000 kD) suggesting that the staircase is due to variable glycosylation of the same core protein. Removal of N-linked sugars does not, however, eliminate all heterogeneity within the band: Two-dimensional nonequilibrium isoelectric focusing gels reveal a series of spots in the 33-kD range at the basic end of the gel.

To confirm that C4/HFBA receptor-inducing activity migrated in the 35-45-kD range, the components of one fraction (fraction 17 in FIG. 1) were separated by SDS-PAGE. Gel slices were homogenized and eluted, and the eluent was chloroform/methanol precipitated to remove SDS prior to bioassay. (Wessel, D. and I.T. Flugge, *Anal. Biochem.* 138:141 (1984)). Although the AChR-inducing activity eluted is reduced approximately tenfold compared with the C4/HFBA material, essentially all of the recovered activity appeared in the same gel slice that contained the protein of interest. The gels were run without reducing agents, since no activity could be recovered following exposure to 50 mM dithiotrheitol or 700 mM β-mercaptoethanol.

EXAMPLE 2

Bioassay of an Active Fraction

A portion of one active fraction (#7) eluted from a C4 reverse phase column eluted with a gradient of isopropyl alcohol in heptafluorobutyric acid (HBFA), as described in Example 1, was dried and the components were separated by SDS-PAGE using a modified Laemmeli protocol. Laemmeli, U.K., *Nature*, 227:68-0685 (1970). The sample buffer did not contain a reductant because such agents destroy AChR inducing activity. The unstained gel was sliced and each slice was homogenized in 0.1 M ammonium bicarbonate - 2.5% SDS and incubated in the same buffer for one hour. Gel fragments were removed by centrifugation, samples were lypohilized, pellets were dissolved in water, and SDS was removed by chloroform/methanol precipitation. Wessel, D. and Flugge, U.I., *Anal. Biochem.*, 138:141-143 (1984). ARIA was assayed by measuring the rate of appearance of new AChRs, with $^{125}$-Iα bungarotoxin (BgTx), 4-5 hours after blocking all exposed receptors with unlabeled BgTx. Myoblasts were plated in 96 well plates, and the assay was performed 4-5 days later as described previously. Usdin, T.B. and G.D. Fischbach, *J. Cell. Biol.*, 103:493 (1986).

EXAMPLE 3

Amplification of a 34-Nucleotide Sequence from Chicken Brain cDNA Using PCR

PCR was performed, as described below, to amplify from chicken brain cDNA a 34-nucleotide sequence (nucleotides 264-297 of Seq. ID #2) that corresponds to the 3' nucleotide of the 7th amino acid codon through the 3' nucleotide of the 18th amino acid codon. The following nested pairs of oligonucleotide primers were used: Each primer contained an EcoRI site at its 5' end. I = inosine.

First pair:
Sense (amino acid residues 1-6 underlined)

5'-GCGGAATTCGA AAI AAI GGI AA(A,G)
GG(A,T,G,C) AA-3' (Seq. ID #4)

Anti-sense (residues 20-23 underlined)

5'-GGCGAATTCATGG ITA I(G,C) (A,T)
(A,T,G,C)GG-3' (Seq. ID #5)

Second pair:
Sense (residues 1-7, underlined)

5'-GCGGAATTCGAAAU AAU GGU AA(A,G)
GG(A,T,G,C) AA(A,G)CC-3' (Seq. ID #6)

Anti-sense (residues 19-23 underlined)

5'-GGCGAATTCATGG ITA I(G,C)(A,T)
(A,T,G,C)GG (T,C)TG-3' (Seq. ID #7)

Poly(A)+ RNA prepared from adult chick brain [Cathala, G. et al., *DNA* 2:329 (1983)] was used as a template for synthesis of cDNA using an oligo(dT) primer and AMV reverse transcriptase [Sambrook, J. et al., *Molecular Cloning: A Laboratory Manual*, 2nd Edition (Cold Spring Harbor Laboratory Press (1989)]. 100 ng of cDNA was subjected to 30 cycles of PCR amplification using the first pair of primers with Tag polymerase under conditions recommended by the manufacturer (Perkin Elmer Cetus). In each cycle denaturation was carried out for 1 min at 94° C., annealing for 2 min at 35° C., and extension for 3 min at 72° C. The amplified DNA was then used as template for 30 more cycles of amplification under the same conditions with the second pair of primers which were longer at their 3' ends.

DNA from the second round of amplification was digested with EcoRI, and fractionated on a 10% polyacrylamide gel. The region of the gel containing DNA of approximately 82 nucleotides (the predicted size of the amplified product, including primer sequence and 5' overhangs) was cut out, and the electroeluted DNA was ligated into the EcoRI site of pBluescript II (Stratagene). DNA from 70 individual plasmid clones was digested with EcoRI and analyzed on a 10% acrylamide gel; 12 clones contained an insert of exactly 82 nucleotides, as determined by comparison with size markers. DNA sequencing confirmed that 3 of these clones encoded amino acids 8-18 of the chemically determined sequence (amino acids 32-42 of Seq. ID #3).

EXAMPLE 4

Screening of Phage from an E18 Chicken Brain cDNA Library

A synthetic oligonucleotide with the sequence (Seq. ID #8) 5'-GCGATGGCTCCCGGCGCC-CCAACCCCCACCACTG-3' (amino acids 8-18) was used to screen 250,000 phage from an E18 chicken brain cDNA library in lambda gt10. The oligonucleotide probe had the same sequence as the 34-nucleotide sequence described in Example 2. The 34-mer was end-labeled with $^{32}P$ using polynucleotide kinase and hybridized to filter replicas of an E18 chick brain cDNA library in lambda gt10). Hybridization was at 50° C. in 0.9 M NaCl, 0.9 M Tris-HCl (ph 8), 6 mM EDTA, 0.1% SDS, 5X Denhardt's, and 500 ug/ml salmon sperm DNA. Washes were at 37° C. in 1X SSC, 0.1% SDS. Positive clones were rescreened once, and subcloned into the EcoRI site of pBluescript II.

EXAMPLE 5

Northern Blot Analysis of Chick-PLP

Total cellular RNA was subjected to electrophoresis (10 ug/lane) in a 1% agarose/2.2M formaldehyde gel and was transferred to Genescreen. The entire spinal cord and brain were dissected free of surrounding tissues, except in adult animals where only the lumbar enlargement of the spinal cord was used. Blots were hybridized at 65° C. in 100 mM NaCl, 1.0 mM EDTA, 5% SDS, 20 mM $Na_2HPO_4$, 50 mM PIPES (pH = 7) with a 2.2 kb $^{32}P$-labeled cRNA that was transcribed from BamH1 - cleaved p65-21 using T3 polymerase according to directions of the manufacturer (Stratagene). Blots were washed at 65° C. in 0.1X SSC, 0.1% SDS, and then at 37° C. in 20 ug/ml RNase A, 0.3 M MaCl, 1 mM EDTA, and 10 mM Tris-HCl (pH 7.5) to reduce background.

EXAMPLE 6

Immunohistochemical Analysis of Chick-PLP

Spinal cords were fixed overnight at 4° C. in 4% paraformaldehyde in PBS, and after impregnation with 30% sucrose (in PBS), 10 um cryostat sections were cut through the lumbar enlargement and thaw-mounted on polylysine-coated slides. Sections were treated with 0.25% acetic anhydride in 0.1 M triethanolamine (pH = 8), and after dehydration in ethanol were hybridized as described previously (6). The anti-sense RNA probe spanned nucleotides 1874-2017 of the ch-PLP cDNA (see FIG. 2), and was transcribed using T3 polymerase from p65-21 that had been linearized with PvuII. Probes were not hydrolyzed before use. Slides were exposed for 8 days.

The monoclonal antibody, referred to as 5.1, was raised against the indicated petpide coupled to soybean trypsin inhibitor and to Keyhole limpet hemocyanin. Supernatants were screened by ELISA with the peptide conjugated to ovalbumin or with partially purified ARIA as the capture antigen. 10 micron frozen spinal cord sections were blocked with 10% goat serum in PBS, incubated in 5.1 supernatant at a dilution of 1:5 in PBS rinsed and, finally, incubated in fluorescein-conjugated goat, anti-mouse antiserum.

EQUIVALENTS

Those skilled in the art will recognize, or be able to ascertain using no more than routine experimentation, many equivalents to the specific embodiments of the invention described herein. Such equivalents are intended to be encompassed by the following claims.

---

I claim:

1. Isolated DNA encoding a protein having the amino acid sequence of FIG. 2 (Seq. ID #3).

2. Isolated DNA having the nucleotide sequence of FIG. 2 (Seq. ID #2).

* * * * *